US006939864B1

(12) United States Patent
Johnson et al.

(10) Patent No.: US 6,939,864 B1
(45) Date of Patent: Sep. 6, 2005

(54) ANIMAL FEED COMPOSITIONS AND METHODS OF USING THE SAME

(75) Inventors: Timothy Robert Johnson, Noblesville, IN (US); Susan Dee Eicher, Lafayette, IN (US); Carrie A. McKee, Wright City, MO (US)

(73) Assignees: Purdue Research Foundation, West Lafayette, IN (US); The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 10/192,762

(22) Filed: Jul. 9, 2002

Related U.S. Application Data

(60) Provisional application No. 60/304,389, filed on Jul. 9, 2001.

(51) Int. Cl.$^7$ ............................................. A61K 31/716
(52) U.S. Cl. ...................................... 514/54; 536/123.1
(58) Field of Search ........................... 424/60; 514/442; 514/54; 536/123.1

(56) References Cited

U.S. PATENT DOCUMENTS

| 4,962,094 | A | * | 10/1990 | Jamas et al. ................... 514/54 |
|---|---|---|---|---|
| 5,147,862 | A | | 9/1992 | Nikl et al. ...................... 514/54 |
| 5,189,028 | A | | 2/1993 | Nikl et al. ...................... 514/54 |
| 5,401,727 | A | | 3/1995 | Rorstad et al. ................ 514/54 |
| 5,487,894 | A | * | 1/1996 | Kovacs ..................... 424/195.1 |
| 5,504,079 | A | | 4/1996 | Jamas et al. ................... 514/54 |
| 5,576,015 | A | * | 11/1996 | Donzis ........................ 424/442 |
| 5,937,790 | A | | 8/1999 | Ito et al. ...................... 119/174 |
| 6,020,324 | A | | 2/2000 | Jamas et al. ................... 514/54 |
| 6,121,464 | A | | 9/2000 | Böttcher et al. ............. 549/222 |
| 6,143,731 | A | * | 11/2000 | Jamas et al. ................... 514/54 |
| 6,214,337 | B1 | | 4/2001 | Hayen et al. ............. 424/93.51 |

FOREIGN PATENT DOCUMENTS

| EP | 0440725 | 6/1994 | ..................... 1/308 |
|---|---|---|---|
| WO | WO 90/04334 | 5/1990 | |

OTHER PUBLICATIONS

Verlhac et al "Immunomodulation by dietary vitamin C and glucan in rainbow trout (*Oncorhynchus mykiss*)", Fish & Shellfish Immunology, 1998, 8, 409-424.*
Chew, B.P. The Journal of Nutrition, Jun. 1995, vol. 125, issue 6, pp. 1804S-1808S.*
Bagni, M., et al., Effect of long term oral administration of an immunostimulant diet in innate immunity in sea bass (*Dicentrarchus labrax*), *Journal of Veterinary Medicine.* Series B, vol. 47(1) 2000:pp. 745-751.
Johnson, T.R., et al., *IFASS Mtg. 2001*, Jul. 25, 2001, Indianapolis, IN, Abstract #1204.
MacLeod, D., et al., Supplemental Vitamin C May Enhance Immune Function in Dairy Cows, *Advances in Dairy Technology*, Western Canadian Dairy Seminar, vol. 8, 1996, pp. 227-235.
McKee, C.A., et al., Ascorbic acid and a Beta-glucan product from *Saccharomyces cerevisiar* influence on dairy calf well-being. Jul. 10, 2000, *J. Anim. Sci.vol. 78 Suppl. 1/ J. Dairy Sci.* 83 Suppl. 1:134 Abstract.
McKee, C.A., et al., Oct. 17-20, 2000, Supplemental Vitamin C and a beta-glucan product enhance dairy calf welfare. *Proceeding of the 34$^{th}$ International Congress of the ISAE: 164 Florinopolis, Brazil*Abstract.
McKee, C.A., et al., Nov. 12, 13 and 14, 2000, Vitamin C and a beta-glucan product effects on neonatal calf immunity. *Proceedings of the Conference of Research Workers in Animal Diseases*:62P Abstract.
McKee, C.A., et al., 2001, Supplemental vitamin C and beta-glucan alter growth and the LPS-induced immunological response in young pigs. *ADSA/ASAS MidWestern meeting.* Des Moines, IA, Abstract.
Soltys, J. et al. Modulation of Endotoxin- and Enterotoxin-induced Cytokine Release by In Vivo Treatment with $\beta$-(1,6)-Branched $\beta$-(1,3)-Glucan, *Infection and Immunity*, Jan. 1999, pp. 244-252.
Verlhac, V., Influence of dietary glucan and vitamin C on non-specific and specific immune responses of rainbow trout (*Oncorhynchus mykiss*), *Aquaculture*, 143 (1996) pp 123-133.
Verlhac, V., Immunomodulation by dietary vitamin C and glucan in rainbow trout (*Oncorhynchus mykiss*), *Fish & Shellfish Immunology* (1998) 8, pp 409-424.
Combating Calf Stress with Antioxidants[online], *Nutrafacts*, 7:1 Roche Vitamins, Inc., 2001 [retrieved on Nov. 18, 2002]. Retrieved from the Internet: <URL:http://www.rochenutrafacts.com/nutrafacts/articles/7_1_calfstress.jsp>.
P. B. Lynch et al., *Effect of Vitamin C (Ascorbic Acid) Supplementation of Sows in Late Pregnancy on Piglet Mortality*, Communication to the Editor, Irish J. of Agricultural Res. 20(2/3):217-219, 1981.
J. A. Roth et al., *In Vivo Effect of Ascorbic Acid on Neutrophil Function in Healthy and Dexamethasone-Treated Cattle*, Am. J. Vet. Res. 46(12):2434-2436, 1985.
J. T. Yen et al., *Response of Swine to Periparturient Vitamin C Supplementation*, J. Animal Science 56(3):621-624, 1983.
Eicher, et al., Modulation of health and production by oral beta-glucan and ascorbic acid after transport. Abstract #328 Journal of Dairy Science, vol. 85, Supplement 1; Journal of Animal Science vol. 80, Supplement 1, p. 82, Jul. 21-25, 2002, Quebec City, Canada.

(Continued)

Primary Examiner—James O. Wilson
Assistant Examiner—Ganapathy Krishnan
(74) Attorney, Agent, or Firm—Greenlee, Winner and Sullivan, P.C.

(57) ABSTRACT

Compositions comprising beta-glucan and ascorbic acid and methods of using the same to improve well-being of animals are provided. The combination of beta-glucan and ascorbic acid exhibit a synergistic effect on the well-being of animals.

20 Claims, No Drawings

OTHER PUBLICATIONS

Eicher, et al., Immunomodulation by oral supplementation of ascorbic acid and beta-glucan to transported dairy calves. Abstract #6 American Society of Animal Science Midwestern Section, American Dairy Science Association Midwest Branch, Mar. 18-20, 2002, Des Moines, IA.

A. Estrada et al., "Immumomodulatory activities of oat B-glucan in vitro and in vivo," Microbiol. Immunol. 41(12): 991-998, 1997.

D.L. Williams, "Overview of $(1 \rightarrow 3)$-$\beta$-D-glucan immunobiology," Mediators of inflammation 6:247-250, 1997.

* cited by examiner

ANIMAL FEED COMPOSITIONS AND METHODS OF USING THE SAME

CROSS-REFERENCE TO RELATED APPLICATIONS

This application claims priority to U.S. provisional application 60/304,389, filed Jul. 9, 2001, which is hereby incorporated in its entirety to the extent not inconsistent with the disclosure herewith.

BACKGROUND OF THE INVENTION

Animals are exposed to many stresses during their lives. These stresses affect the health of the animal, the growth of the animal, and overall well-being. Currently, antibiotics and other treatments are used to improve the immune function of animals. Concerns over antibiotic use in animal production has created a need to find more natural immunostimulants.

Beta-glucans are linked polysaccharides and are a component of yeast cell walls. Beta-glucan has been reported as a dietary supplement for aiding digestion and reducing cholesterol levels in animals and humans (EP 0440725 B 1, Jun. 1, 1994). Beta-glucan has also been reported as useful for reducing weight gain or enhancing weight loss (U.S. Pat. No. 6,020,324, Feb. 1, 2000). Beta-glucan has been reported to increase the high density lipoprotein cholesterol level in mammals (U.S. Pat. No. 6,143,731, Nov. 7, 2000). Beta-glucan has been reported as a component in animal feed to enhance the growth rate of an animal (U.S. Pat. No. 6,214,337, Apr. 10, 2001). Beta-glucan has also been reported to be useful in enhancing the efficacy of a fish vaccine (U.S. Pat. No. 5,147,862, Sep. 15, 1992; U.S. Pat. No. 5,401,727, Mar. 28, 1995; U.S. Pat. No. 5,189,028, Feb. 23, 1993).

Vitamin C (ascorbic acid), an anti-oxidant, has been generally reported to stimulate immune response. The effect that vitamin C and glucan have on the immune function in fish has been studied (Fish & Shellfish Immunology (1998) 8, 409–424; Aquaculture 143 (1996) 123–133).

An improved method of strengthening the immune system and improving the well-being of animals is needed.

BRIEF SUMMARY OF THE INVENTION

This invention provides compositions and methods of using those compositions to improve the well-being of animals. "Well-being" includes enhancement in one or more of the following: weight gain, efficiency of growth, behavior, disease resistance, reduced stress from management and environment and/or immune function.

Provided is a composition comprising an effective amount of beta-glucan and an effective amount of ascorbic acid to improve well-being of an animal. More particularly, the effective amount of beta-glucan is between about 0.1 to about 1 mg beta-glucan/kg of body weight (BW) per day, more preferably between about 0.2 to about 0.8 mg beta-glucan/kg of body weight (BW) per day and the effective amount of ascorbic acid is between about 50 to about 1000 mg ascorbic acid/kg of feed per day, more preferably between about 250 to about 500 mg ascorbic acid/kg of feed per day and all useful intermediate ranges and values therein. One effective amount of the composition is 0.044 to about 0.088% by weight of dry milk replacer/day. The composition may be used as a feed additive or otherwise consumed by animals and may also be administered directly into the body, for example as an injection, provided it is purified sufficiently. The amount of the composition used in the feed can be any suitable portion of the total dietary intake, as long as the well-being is improved. For example, the additive can comprise from about 2 to about 4% by weight of the total dietary dry matter intake, or other effective amounts. One presently preferred composition is used to feed calves, where the calves are fed 10% of their body weight per day. Of this amount, 12.5% is dry milk replacer. 0.3% of the intake is beta-glucan. 250 mg of Vitamin C is added to the dry milk replacer twice daily.

Also provided are methods of using the compositions of the invention, comprising administering an effective amount of said composition to an animal.

DETAILED DESCRIPTION OF THE INVENTION

Cattle and porcine are the presently preferred animals to be treated using the compositions and methods of the invention. However, other animals, including other mammals and non-mammals may be treated, including avian species. The animals may be treated at any stage of life, for example, right after birth and through adulthood. The methods described herein can be used in an analogous manner in other animals not specifically mentioned herein, as known in the art without undue experimentation. The present invention is intended to include compositions, use of the compositions and methods described herein to enhance well-being in all other animals, where such use in not already known in the art.

Actual amounts of components in the compositions that are useful to improve well-being may be determined without undue experimentation using the methods described herein, as well as methods known in the art, without undue experimentation. The compositions may contain components other than those specifically exemplified herein, such as other vitamins, minerals and drugs, as well as other components known in the art.

Any suitable form of beta-glucan and ascorbic acid, from any suitable source may be used, as known in the art. One useful beta-glucan product is derived from yeast or grains, but not limited to, yeast, any yeast derivatives such as yeast cell-wall concentrate, barley, oats, distillers, grains (wet or dry), brewers grains, and products derived from liquid by-product feed streams produced at breweries, distilleries, and fuel ethanol plants and mixtures with beta-glucan concentrates that have been purified from yeast cell-wall material. A presently-preferred form of beta-glucan used is NUTRI-FERM ENERGY PLUS™ (Natural Chem Industries, Ltd., Houston, Tex.), which is derived from yeast. A presently-preferred form of ascorbic acid is STAY-C 35™ (ascorbyl-2-polyphosphonate) (a protected ascorbic acid) (Roche Vitamins, Inc., Parsippany, N.J.).

Immune function is monitored as known in the art. Improvement in immune function is determined by methods known in the art. Acute phase proteins (fibrinogen, haptoglobin), neutrophil phagocytosis and chemiluminescence, plasma IgG, and interferon-gamma RNA expression of Interleukin-1 and its receptor antagonist in Bronchial Alveolar Lavage Cells are some of the indicators of immune function measured.

Animal feed protocols such as amount of feed given and timing of feeding is known in the art. One preferred timing of feeding is twice daily. The compositions of the invention can be used in milk replacers, water or solid foods, for example, as known in the art. The length of time the compositions are administered is selected to achieve the desired improvement in well-being. The useful length of time the compositions are administered is easily determinable by one of ordinary skill in the art without undue experimentation. The compositions may be administered during periods of stress or before periods of stress, for example. Some stresses include transport, indoor caging and other events and conditions, as known in the art. When the compositions are used as supplements outside of feeding, routes of administration and frequency of administration are easily determinable by one of ordinary skill in the art without undue experimentation. If the composition is administered as injection, it must be purified and sterilized, as known in the art.

The statistical analysis herein uses the p-value as a measure. The p-value is known in the art. A low p-value indicates there is a correlation between the treatment and the variable. A high p-value indicates there is no correlation between the treatment and the variable.

Porcine Study

The objective of this study was to evaluate the potential benefit of supplementing the neonatal pig with Vitamin C (VC) and/or Beta-glucan (BG). Thirty-two crossbred pigs were selected at birth and assigned to one of four dietary treatment groups (n=8/group). Beginning on the day of birth, pigs received their respective treatments via an oral gavage on a daily basis until weaning at 2 weeks of age. Dietary treatment groups included Control (Con; no VC or BG), VC (75 ppm), BG (0.312 g/kg body weight) and VC+BG (75 ppm and 0.312 g/kg body weight). After weaning, pigs were placed on a starter ration containing their respective dietary treatments and a Phase 1 diet specific for the University of Missouri Swine unit for a 2 week period. Body weights were recorded every 3 days to adjust dietary treatment doses. On day 14 postweaning, blood samples were collected at 30-min intervals for one hour followed by an I.V. injection of lipopolysaccharide (LPS; 150 ug/kg). LPS is part of bacterial cell walls that initiates the immune response. Blood samples were collected at 30-min intervals for an additional 3-hour period following the LPS challenge. Blood samples were analyzed for serum cortisol (CS), ACTH and tumor necrosis factor-alpha (TNF) which are indicators of acute stress response to challenge (LPS).

A time x treatment interaction (P=0.0002) was observed for body weight. The pigs receiving the VC+BG had greater body weights than the Con (P<0.017) and VC (P=0.009) pigs and the BG pigs tended to have greater body weights than the Con (P=0.09) and the VC (P=0.05) pigs. There was no effect of dietary treatment (P<0.26) on basal ACTH, CS or TNF. There was also no measurable effect (P<0.86) of dietary treatment on the ACTH response to the LPS challenge because the ACTH likely increases and decreases in less time than the span of the measure. However, there was a dietary treatment effect (P<0.045) on the CS response to the LPS challenge. The CS response was lower (P=0.005) in the VC group as compared to the Con group, and the CS response tended (P<0.09) to be lower in the BG and VC+BG groups as compared to the Con group. A time x dietary treatment effect (P<0.028) was observed for the TNF response to the LPS challenge which can be primarily attributed to the more rapid decline in serum TNF for the VC group. The data demonstrate that the inclusion of VC and/or BG do indeed alter piglet growth and the response to an endotoxic challenge.

Calf Study

Materials and Methods

Once the calves are removed from the dam they received a superior colostrum diet for three days. Three days after they were born, calves were started on all milk, milk replacer. The calves were assigned randomly to one of four treatment groups control, β-glucan, Vitamin C, and β-glucan and Vitamin C. Each treatment is represented in a block (1 block has 4 calves and each room has 3 blocks). Initial weight and temperature were taken when calves were placed on study, then weekly for six more weeks.

Fecal scores, nasal and ocular discharges were recorded daily along with room temperature and humidity. Blood samples were taken every week for seven weeks; 10 ml heparinized tube for plasma to measure cortisol and ascorbic acid; 5 ml sodium citrate tube for hematocrits, granulocytes, lymphocytes and fibrinogen.

Calves were fed milk replacer equaling 10% of their body weight per day, which was given in two equal rations (morning and afternoon). Dry milk replacer was equal to 12.5% of amount fed. Calves on treatment 2 and 3 were given β-glucan equaling 0.3125% of total intake. Calves on treatment 3 and 4 received 250 mg of Vitamin C twice a day.

At week 3 and 6 an additional 10 ml heparinized tube of blood was collected to measure IgG, TNF-α, IFN-γ and haptoglobin. At week 3 and 6, a whole blood assay was performed to determine the phagocytosis and chemiluminescence capacity of neutrophils. At week 6 a lung lavage was performed to collect macrophages. Total RNA was extracted for RT-PCR amplification to determine IL-1, IL-1Ra, and TNF expression.

Video cameras were set up in each room to observe calves (12 calves per room). Behavior was recorded six days per week to look for increased activity or alertness, any behavior indicating that the calf was or was not feeling well (feeding and drinking at normal rates).

Results:

All data are reported for control (C), Beta-glucan (Energy Plus, Bg), ascorbic acid (STAY-C, AA), and Both (Stay-C and Energy Plus)±SE, respectively, (P<0.01). Body weight (BW) change showed a significant interaction between BG and AA. Mean BW change was 1.81±0.12, 1.96±0.12, 1.48±0.12, and 2.32±0.12 kg/wk.

Fecal scores showed a BG and AA interaction, mean fecal scores were 1.381.03, 1.55±0.03, 1.48±0.03, 1.38±0.03, (P<0.01). Fecal scores are measured on a scale of 1–4, with 1=solid and 4=fluid. Hematocrit values showed a main effect of BG and an interaction of BG and AA (P<0.01; 29.641.22, 29.681.22, 30.48#0.22, and 28.47±0.22). Hematocrit is a measure of cell pack volume. A high value of hematocrit indicates dehydration. A reduction in hematocrit for calves supplemented with BG+AA (IG) suggests greater hydration and plasma volume. This is consistent with reduced fecal score (diarrhea). Granulocytes, temperature, nasal and ocular discharge were not significantly different. Lymphocyte percent tended to increase (P<0.10), for AA compared to control calves (74.35, 72.35, 71.03, and 71.57±0.63, for AA, BG, Con, and IG, respectively) Fibrinogen concentrations showed a BG and AA interaction. Mean fibrinogen was 411.09±12.91, 456.92±12.91, 442.34±12.91, and 416.47112.91 mg/dl (P<0.01). Fibrinogen is an acute phase protein released in response to immune challenge. The blood measurements were performed by standard methods known in the art.

This study indicates that supplemental ascorbic acid and P-glucan synergistically improve weight gain, health status, and overall well-being of dairy calves.

Transport Study

The effect on transport stress of animals of adding beta-glucan and ascorbic acid to calves' diet was studied. Calves (n=39) were blocked by sex and assigned to treatments; (IG) 113 g of a yeast cell wall derivative (Energy-plus, Natural Chem Industries, LTD) and 250 mg of an ascorbic acid product (Stay-C, Roche Vitamins), (BG) 150 mg of 13-glucan fraction from yeast cell-walls that is equivalent to that contained in Energy-plus (Biopolymer Engineering, MN) plus 250 mg Stay-C, or (Con) a positive control with no supplements, but 1 L subcutaneous electrolytes. Calves were fed an all milk, milk replacer at 4.45 kg/d in 2 equal feedings with supplements in the milk replacer. A grain based dry feed was offered beginning on d 3. Calves, 3 to 10 d-of-age, were transported for 4 h, after being weighed and sampled by jugular veni-puncture, then calves began treatments in outdoor hutches. Weights were taken weekly for 4 wk and feed weighed back every other day. Fecal and clinical scores, and nasal and ocular discharge occurrences were recorded 3 times per wk. Blood samples were collected 0 h then d 3, 7, 10, 14, 21, and 28 post-transport. Data were analyzed as a repeated measures design using the General Linear Models (GLM) procedures of SAS (Cary, N.C.). Although weights were not different among calves, intake at week 4 was less ($P<0.05$) for IG (1.68 kg/d) than for Con (2.66 kg/d). Feed efficiency, kg feed/kg gain, was improved ($P<0.05$) for IG (0.412) and tended ($P<0.10$) to improve for BG (0.4876) at wk 4 compared to Con (0.835). Plasma IgG, fecal and clinical scores, serotonin, and tryptophan were not different ($P>0.10$). Ocular and nasal discharge scores were greater for BG than for IG during wk 2 ($P<0.05$). This coincided with peripheral blood mononuclear cell counts that were least for BG compared to IG and Con on d 10 samples and IG greater than Con (d 3), and BG (d 21 and 28) ($P<0.05$). Total discharge (over all weeks) tended ($P=0.08$) to be lower for IG (0.714 occurrences) than Con or BG (1.77 and 2.9 occurrences, respectively). Plasma fibrinogen, mg/dl, tended ($P<0.10$) to be greater on d 7 for IG (510.2) than Con (443.2) and than BG on d21 (510.4 and 450.7 for BG and Con, respectively). Hematocrit percentages were least ($P<0.05$) for BG (27.2%) compared to IG (31.9%) post-transport and on d-21 and compared to IG ($P<0.05$) and Con ($P<0.10$) on d 10 (27.6, 34.0, and 33.0 for BG, Con, and IG, respectively) and both IG and Con on d 28 post-transport (32.6, 34.0, and 27.9; $P<0.05$). Leukocyte numbers were least for BG compared to IG on d 21 (9.1 vs 12.2, $P=0.06$) and d 28 (10.2 vs 14.5, $P<0.05$). On d 21 post-transport, granulocyte numbers tended to be greater ($P=0.08$) for IG calves than for BG calves (4.5 vs $2.6 \times 10^9$ cells/ml). Percentage of neutrophils positive for high CD 18 expression was greater in the IG calves than for those of the BG or Con calves on d 28 (13.9, 7.5, and 8.3%, respectively). Neutrophil phagocytosis was reduced in BG calves compared to Con ($P<0.05$) and IG ($P<0.10$) calves on d 28 (32.6, 62.1, and 55.6%, respectively) and chemiluminescence was least in BG calves compared to the Con calves on d 28 (25.7 and 52.8%, respectively). These data showed that modulation by the supplements on innate immunity are not evident until 28 d post-transport, but then the yeast cell-wall derivatives differed in their effectiveness. Both beta-glucan products were beneficial for feed efficiency by wk 4.

Although the description above contains many specificities, these should not be construed as limiting the scope of the invention, but as merely providing illustrations of some of the presently-preferred embodiments of the invention. For example, amounts of beta-glucan and vitamin C other than those specifically mentioned may be used. All references cited herein are incorporated by reference to the extent not inconsistent with the disclosure herein. All numerical ranges listed herein include all useful intermediate ranges and all useful individual values therein.

What is claimed is:

1. A composition comprising about 0.1 to about 1 mg yeast-derived beta-glucan/kg of body weight and about 50 to about 1000 mg ascorbyl-2-polyphosphonate/kg of feed to enhance the well-being of a mammal.

2. The composition of claim 1, comprising about 0.2 to about 0.8 mg yeast derived beta-glucan/kg of body weight and about 250 to about 500 mg ascorbyl-2-polyphosphonate/kg feed.

3. The composition of claim 1, wherein the composition further comprises milk replacer.

4. The composition of claim 1, wherein the feed further comprises dry feed.

5. The composition of claim 1, further comprising at least one mineral or vitamin which is not ascorbic acid.

6. A mammal feed additive comprising about 0.1 to about 1 mg yeast derived beta-glucan/kg of body weight and about 50 to about 1000 mg ascorbyl-2-polyphosphonate/kg of feed wherein the amount of the additive is from about 2 to about 4% by weight of the total dietary dry matter intake daily.

7. The mammal feed additive of claim 6, comprising about 0.2 to about 0.8 mg yeast derived beta-glucan/kg of body weight per day and about 250 to about 500 mg ascorbyl-2-polyphosphonate/kg body weight per day.

8. The mammal feed additive of claim 6, wherein the additive comprises dry feed.

9. The mammal feed additive of claim 6, wherein the additive further comprises milk replacer.

10. The mammal feed additive of claim 6, further comprising at least one mineral or vitamin which is not ascorbic acid.

11. A method of enhancing weight gain in a mammal comprising administering an effective amount of yeast derived beta-glucan and an effective amount of ascorbyl-2-polyphosphonate to said mammal.

12. The method of claim 11, wherein said effective amount contains about 0.1 to about 1 mg yeast derived beta-glucan/kg of body weight per day and about 75 to about 500 mg ascorbyl-2-polyphosphonate/kg of body weight per day.

13. The method of claim 11, wherein said effective amount contains about 0.2 to about 0.8 mg yeast derived beta-glucan/kg of body weight per day and about 250 to about 500 mg ascorbyl-2-polyphosphonate/kg of body weight per day.

14. The method of claim 11, wherein said mammal is cattle.

15. The method of claim 11, wherein said mammal is a bos tarus or bos indicus.

16. The method of claim 11, wherein said mammal is porcine.

17. A method of enhancing weight gain in a mammal comprising administering an effective amount of yeast derived beta-glucan and an effective amount of ascorbyl-2-polyphosphonate to said mammal.

18. The method of claim 17, wherein said mammal is cattle.

19. The method of claim 17 wherein said mammal is a bos tarus or bos indicus.

20. The method of claim 17, wherein said mammal is porcine.

* * * * *

UNITED STATES PATENT AND TRADEMARK OFFICE
CERTIFICATE OF CORRECTION

PATENT NO.    : 6,939,864 B1
DATED         : September 6, 2005
INVENTOR(S)   : Johnson et al.

It is certified that error appears in the above-identified patent and that said Letters Patent is hereby corrected as shown below:

<u>Column 4,</u>
Line 42, replace "1.381.03" with -- 1.38±.03 --.
Line 45, replace "29.641.22" with -- 22.64±.22 --.
Line 46, replace "29.681.22, 30.48#0.22," with -- 29.68±.22, 30.48±.22, --.
Line 58, replace "416.47112.91" with -- 416.47±12.91 --.

Signed and Sealed this

Fourth Day of April, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,939,864 B1 | Page 1 of 1 |
| APPLICATION NO. | : 10/192762 | |
| DATED | : September 6, 2005 | |
| INVENTOR(S) | : Timothy Robert Johnson, Susan Dee Eicher and Carrie A. McKee | |

It is certified that error appears in the above-identified patent and that said Letters Patent is hereby corrected as shown below:

Col. 1, Line 11, add --STATEMENT REGARDING FEDERALLY SPONSORED RESEARCH OR DEVELOPMENT
This invention was made with government support under a contract awarded by the USDA. The government has certain rights in the invention.--

Signed and Sealed this

Sixteenth Day of June, 2009

JOHN DOLL
*Acting Director of the United States Patent and Trademark Office*